United States Patent [19]

Dieken et al.

[11] Patent Number: 5,411,534
[45] Date of Patent: May 2, 1995

[54] ELECTRICAL SAFETY SYSTEM FOR ELECTRICAL DEVICE

[75] Inventors: Alan P. Dieken, Oakdale; David J. Fischer, Arden Hills; Jonathan C. Platt, Bloomington; William L. Sondermann, Circle Pines, all of Minn.

[73] Assignee: Minnesota Mining and Manufacturing Company, St. Paul, Minn.

[21] Appl. No.: 274,353

[22] Filed: Jul. 13, 1994

Related U.S. Application Data

[63] Continuation of Ser. No. 8,724, Jan. 22, 1993, abandoned.

[51] Int. Cl.$^6$ .............................................. A61B 5/00
[52] U.S. Cl. ....................................... 607/31; 128/908
[58] Field of Search .................... 128/908; 607/31; 29/753; 340/547, 573

[56] References Cited

U.S. PATENT DOCUMENTS

| | | | |
|---|---|---|---|
| 4,109,223 | 8/1978 | Tenkman et al. | 128/908 |
| 4,298,863 | 11/1981 | Natitus et al. | 340/573 |
| 4,338,951 | 7/1982 | Saliga | 128/908 |
| 4,578,628 | 3/1986 | Siwak | 320/2 |
| 4,598,281 | 7/1986 | Maas | 128/908 |
| 4,687,004 | 8/1987 | Zenkich | 128/908 |
| 4,715,385 | 12/1987 | Cudahy et al. | 128/710 |
| 4,763,663 | 8/1988 | Uphold et al. | 128/671 |
| 4,803,996 | 2/1989 | Peel et al. | 128/710 |
| 4,872,139 | 10/1989 | Okamoto et al. | 365/52 |
| 4,888,864 | 12/1989 | Masaki | 29/753 |
| 5,010,889 | 4/1991 | Bredesen et al. | 128/715 |
| 5,044,365 | 9/1991 | Webb et al. | 607/31 |

FOREIGN PATENT DOCUMENTS

| | | | |
|---|---|---|---|
| 0488410A1 | 6/1992 | European Pat. Off. | A61B 5/0432 |
| 3036217A1 | 4/1982 | Germany | G08C 17/00 |
| 3701492 | 7/1987 | Germany | G11B 33/10 |
| 8911113 | 12/1989 | Germany | A61B 7/04 |

*Primary Examiner*—George Manuel
*Attorney, Agent, or Firm*—Gary L. Griswold; Walter N. Kirn; John H. Hornickel

[57] ABSTRACT

Apparatus and electrical circuitry are provided for electrical devices in order to provide electrical isolation of exposed electrical contacts on at least one of multiple modules of the electrical device. The apparatus includes at least one actuating component in one module and at least one sensor component within a second module in electrical communication with electrical circuitry, whereby electrical isolation of the exposed electrical contacts ceases when the sensor apparatus senses a desired location of the module. Placement of the apparatus and electrical circuitry to reside within the modules promotes electrical safety while minimizing tampering with safety aspects of the device. The apparatus and circuitry are useful for medical devices such as handheld diagnostic devices and consumer devices such as telephones.

17 Claims, 4 Drawing Sheets

ELECTRICAL SAFETY SYSTEM FOR ELECTRICAL DEVICE

This is a continuation of application Ser. No. 08/008,724, filed Jan. 22, 1993, abandoned.

FIELD OF THE INVENTION

This invention relates to an electrical safety system for electrical devices, and especially for medical devices to be used in the proximity of health care practitioners and patients.

BACKGROUND OF THE INVENTION

An electrical device, such as a medical device requiring the use of electricity, must comply with certain electrical safety requirements in order to achieve listing with organizations that review the safety of electrical products. A concern present for any medical device is to minimize the possibility of electrical shock caused by exposure to electrical contacts used as part of the medical device. This concern has caused the art to develop electrical circuitry such as isolation amplifiers and the like to minimize the exposure of the patient and health care practitioner to electrical voltage and current. See, for example, U.S. Pat. No. 4,803,996 (Peel et al.).

Other electrical circuitry has been developed in the circumstance when the medical device comprises two or more separable modules which require electrical contact when the modules are mated for battery-powered use. See, for example, U.S. Pat. No. 4,578,628 (Siwiak), which uses switching and fusing means to assure proper interconnection between a battery pack and its mateable radio portion and avoidance of inadvertent short circuits of the battery terminals.

Medical device market suppliers and users, in conjunction with Underwriters Laboratories, have developed safe operating performance criteria for medical apparatus that limit exposed electrical contact of apparatus to an extremely small electrical current should a person come in contact with these exposed contacts. Currently, the Underwriters Laboratories Standard for Safety 544 sets a limit of 50 microamps for double insulation circuits and otherwise 100 microamps.

Electronic medical devices often must be made small and portable. Examples include stethoscopes and other diagnostic systems, electronic prosthetic devices such as transcutaneous electrical nerve stimulators, and patient monitoring equipment. While this list is not exclusive, it generally indicates the problems which are associated with designing and producing small, portable electronic medical devices.

Requirements for such electronic medical devices can include a light-weight, portable diagnostic device having a self-contained power source (often a rechargeable battery) capable of easy and safe operation. Stationary accessory operations for such electronic medical devices typically include battery recharging apparatus and circuitry and data communication to associated computers, instruments and equipment. The mechanical alignment and electrical interconnection between the portable device and the stationary device must be convenient and safe in the critical hospital and clinical environments. These requirements are especially true of electronic stethoscopes and portable, hand held diagnostic tools such as cardiac and pulmonary auscultation detectors and graphic display apparatus.

Two examples of portable electronic medical devices having multiple modules comprising a portable diagnostic module and a stationary supporting module include stethoscopes and associated equipment disclosed in U.S. Pat. No. 5,010,889 (Bredesen et al.) and pending U.S. patent application Ser. No. 07/782,079 (Bredesen et al.), the disclosures of which are incorporated by reference.

Exposed electrical contacts are often required for making effective connections between portable devices and associated support equipment, such as a portable medical device containing a battery and the associated battery charger. Electrical safety can be achieved in various ways. Some prior efforts have included limiting the level of operating voltage, (e.g., operating below a certain threshold such as 40 volts) under carefully specified conditions as covered by Standard 544 from Underwriters Laboratories, Inc., Northbrook Ill. or providing insulation or clearances that limit leakage current to low levels and limit exposed contact points to voltages below specified levels.

SUMMARY OF THE INVENTION

The invention provides both apparatus and circuitry for electrical isolation of exposed contacts on at least one of multiple modules of electrical devices when such contacts are not in use. Electrical isolation can include either electrical disconnection or electrical grounding, or both, as the electrical device may require for safety purposes. The invention also provides means for connecting contact points to active electrical circuitry only during the time that there is proper mechanical alignment between two modules of a medical device. A nonlimiting example of two modules of a medical device is a portable diagnostic device separably electrically connected to and mechanically aligned in proximity to stationary support equipment which is typically connected to an electrical line power.

In another aspect of the present invention, apparatus and circuitry means for switching the electrical circuit is provided where the apparatus and circuitry is controlled only by positioning the portable device in proper orientation with, and in proximity to, the support equipment device by means of a system that is not apparent to the user or subject to user intervention.

In another aspect of the invention, the apparatus and circuitry means only energizes the electrical contact points after mechanical alignment. The contact points reside at a location of the portable module's mechanical alignment with the stationary support equipment, such that a health care practitioner or a patient is protected from exposure to such energized electrical contact points.

The invention provides an apparatus for electrical isolation of exposed electrical contacts on at least one of multiple modules of an electrical device. The apparatus comprises at least one sensor component within at least one module in electrical communication with electrical circuitry, whereby electrical isolation of the exposed electrical contacts ceases when each sensor component senses a desired location of the module and the exposed electrical contacts become energized.

The invention also provides an electrical circuit for electrical isolation of exposed electrical contacts on at least one of multiple modules of electrical devices. The circuit comprises at least one electrical switching device in electrical communication with at least one sensor component within one module, whereby electrical isolation of the exposed electrical contacts ceases when the sensor component senses a desired location of the module and at least one switching device closes.

A feature of the invention is the economical employment of apparatus and circuitry within the stationary support equipment which is self-contained and promotes safety.

Another feature of the invention is the provision of the circuitry to maintain open circuits unless and until there is proper mechanical alignment contact between the portable module and the stationary support equipment. In that manner, the electrical isolation of exposed electrical contacts on at least one module of the device is maintained until the electrical isolation ceases due to proper mechanical alignment.

An advantage of the invention is that the likelihood of exposed, energized, electrical contacts on the stationary support equipment is minimized to the circumstance when the portable module is in proper mechanical alignment and in electrical interconnection. The portable module in proper mechanical alignment then shields the energized contacts from exposure.

The foregoing advantages, construction and operation of the present invention will become more readily apparent from the following description and accompanying drawings.

EMBODIMENTS OF THE INVENTION

Electrical devices useful with the apparatus of the present invention can be electrical devices where a first module is portable and rechargeable, and the second module is stationary and electrically connectable to line power. Nonlimiting examples of electrical devices include handheld consumer devices (such as flashlights, electric razors, electronic control units, cordless and cellular telephones, and portable, electrical hand tools), larger portable electrical equipment (such as lawn and garden equipment), and other modules requiring temporary electrical connection to a stationary module.

Figure 1:
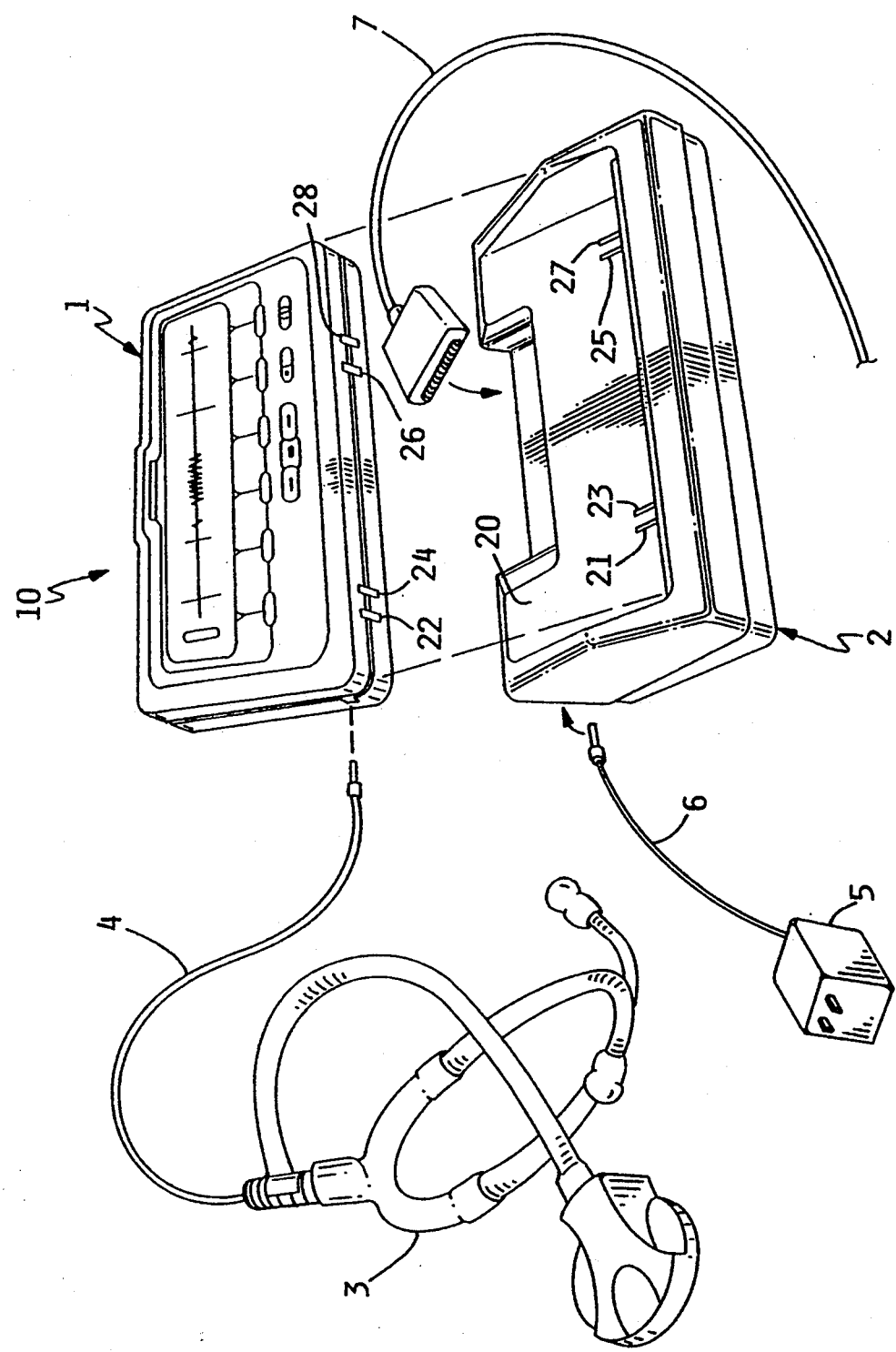
FIG. 1 is a perspective view of a medical device including a stethoscope, a portable display module, a stationary printer/charger module, and electrical line power source (including a transformer) utilizing the present invention.

Preferably, electrical devices are medical devices where portability of handheld diagnostic equipment is desirable. The medical device shown in FIG. 1 is a graphical auscultation system 10 to be used by doctors or other medical practitioners for the acquisition, display, storage and analysis of body sounds, particularly heart sounds. Nonlimiting examples of such auscultation instrumentation are graphic display stethoscopes disclosed in U.S. Pat. No. 5,010,889 (Bredesen et al.) and pending U.S. patent application Ser. No. 07/782,079 (Bredesen et al.), the disclosures of which are incorporated by reference.

The system 10 includes stethoscope 3 which the health care practitioner uses to select the appropriate sound location and characteristic. Integral to the stethoscope 3 is a transducer (not shown) which converts the acoustical signal to an electrical signal. The electrical signal is communicated by means of cable 4 to the portable, hand held display module 1. The display module 1 may include a complex electronic processing circuitry as well as a liquid crystal or other display and memory and other electrical components, all powered by an internal battery, preferably a rechargeable battery.

Electrical and data communication and other support service for the portable display module 1 is provided from the printer/charger module 2 which is powered from a standard electrical line power source 5 through a connecting cable 6. Further, communication to other devices such as a computer printer, a personal computer or other accessories (all not shown) can be made through interconnection cable 7.

Figure 2:
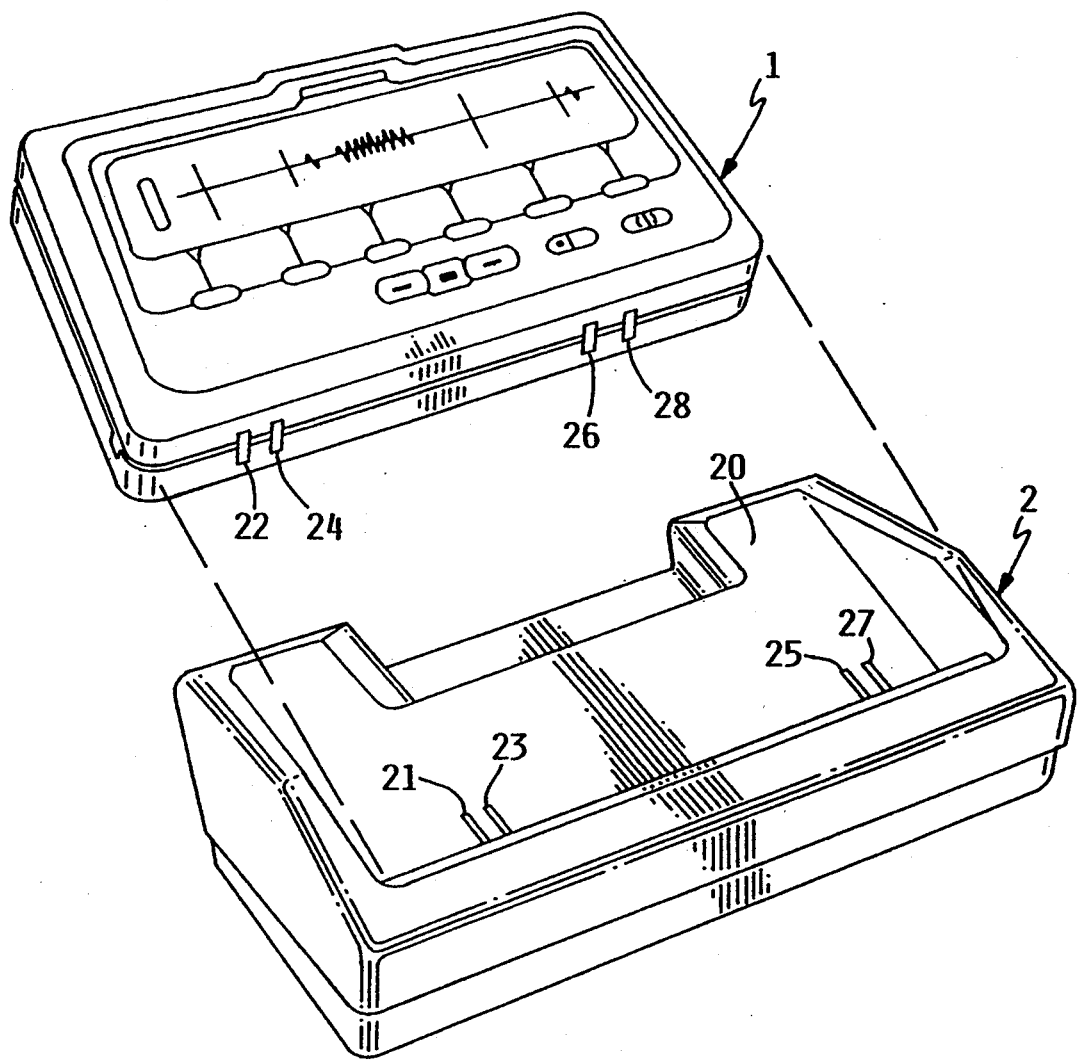
FIG. 2 is a perspective view of the display module and the printer/charger module showing exposed electrical contact pairs.

The stationary printer/charger module 2 is readily accessible and made electrically safe for use by means of the present invention. FIG. 2 shows detail of the electrical interconnection of the display module 1 and printer/charger module 2. Electrical contact pairs 21-22 and 23-24 are data communication connections and contact pairs 25-26 and 27-28 are the battery charging connections. Electrical contact is made between these respective contact pairs when the display module 1 is properly mechanically aligned, e.g., positioned and seated into recess 20 of the printer/charger module 2.

In preferred use, the printer/charger module 2 is connected to line power by cable 6 and power source 5 and to remote equipment through cable 7.

According to the invention, connector contacts 21, 23, 25, and 27 are electrically isolated from the other circuitry of the printer/charger module at all times except when the display module is seated in the printer/charger module 2 for charging and/or data transfer.

Figure 3:
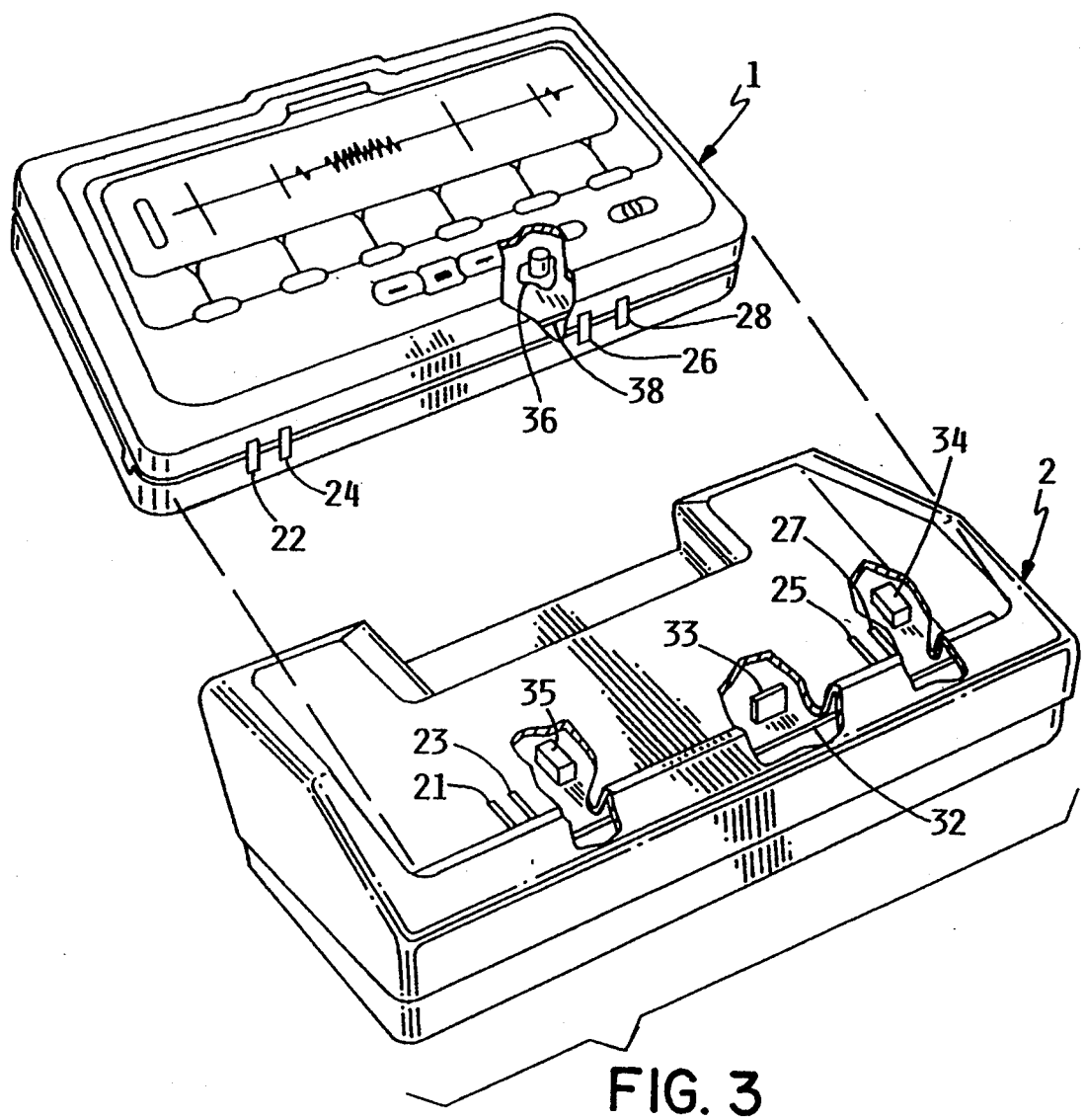
FIG. 3 is a perspective view with a partial cutaway of the display module showing the actuator component for the safety system in juxtaposition with a partial cutaway of the printer/charger module showing the safety switching components.

Preferably, the electrical isolation is accomplished by providing switching devices, (e.g., solid state switches, electrical relays, and the like) As shown in FIG. 3, normally open electrical relays 34 and 35 are provided in the electrical circuit of the printer/charger module 2 in electrical communication with contacts 26 and 28, and 25 and 27, respectively.

Operation of relays 34 and 35 to close electrical circuitry between printer/charge module 2 and display module 1 is accomplished by a sensor component 33 which is only operative by properly seating the display module 1 in the printer/charger module 2, thereby aligning actuating component 36 with the sensor 33. Electrical isolation ceases when normally open relays 34 and 35 close.

Figure 4:
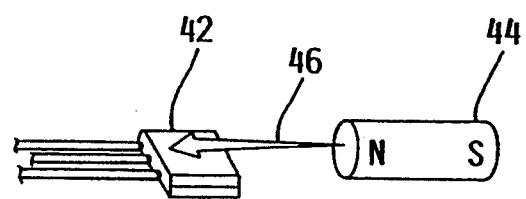
FIG. 4 is a perspective of the actuator and sensor showing the relative operational orientation.

Preferably, the sensor component 33 is a magneto-resistive sensor mounted on a electrically insulating circuit board 32 within printer/charger module 2. Preferably, the actuating component 36 is a permanent magnet mounted on a electrically insulating circuit board 38 in the display module. Specifically the magnet is model 102MG15 magnet and the magneto-resistive digital position sensor is a model 2SSP sensor, both commercially available from Micro Switch Division of Honeywell Inc., Minneapolis Minn. The relative magnetic alignment of these components is shown in FIG. 4 wherein the magnet 44 is positioned in a plane parallel to the plane of the magneto-resistive sensor 42 and aligned with the sensor. Magnet 44 can be oriented in either polarity. Preferably, arrow 46 indicates the locus of influence of the magnet field. The sensor-to-magnet operational range is approximately 2.5 cm or less, and preferably 0.5 cm when the modules 1 and 2 are in proper alignment.

Preferably, the apparatus and circuitry are contained within the modules and concealed from sight. Thus, no part of the safety system is apparent to the user. Thus, operation of the safety system it is not readily apparent to the user making it difficult to override or circumvent the safety system. Further, the use of obscured magnetic components reduces the possibility of overriding the safety system with commonly available materials applied to the exterior of either module 1 or 2. Materials, such as tape, string, or adhesives could otherwise restrain exterior components in undesired positions for unsafe use. Procedures such as using a wire cutter for disconnecting exterior components are minimized by use of the safety system of the present invention.

Numerous combinations of actuating component 36 and sensor component 33 can be used in place of the presently preferred magneto-resistive/permanent-magnet combination. Nonlimiting examples include magnetic Hall-effect sensor/permanent-magnet, reed-switch/permanent-magnet, optical switch/light emitting diode (LED) light source, magneto-dynamic transformer, electro-static capacitive coupling, electro-dynamic capacitive coupling, and radio frequency coupling, or other solid state sensors. Further, multiple actuator-sensor pairs could be used in selected geometric configuration and/or selected switching logic configuration to provides successively higher security levels through successively more specific positioning or order of positioning events.

Multiple sensor components and multiple actuator components also can be employed in either or both modules according to desired advantages, e.g., to use multiple sensor components and actuator components to identify and recognize differentiated modules for specific interaction between modules; and to use multiple sensor components in one module to differentiate among different actuator components in different mating modules. In that respect, use of multiple sensor components and multiple actuator components provides an additional level of safety control or communication technique, or both.

Figure 5:
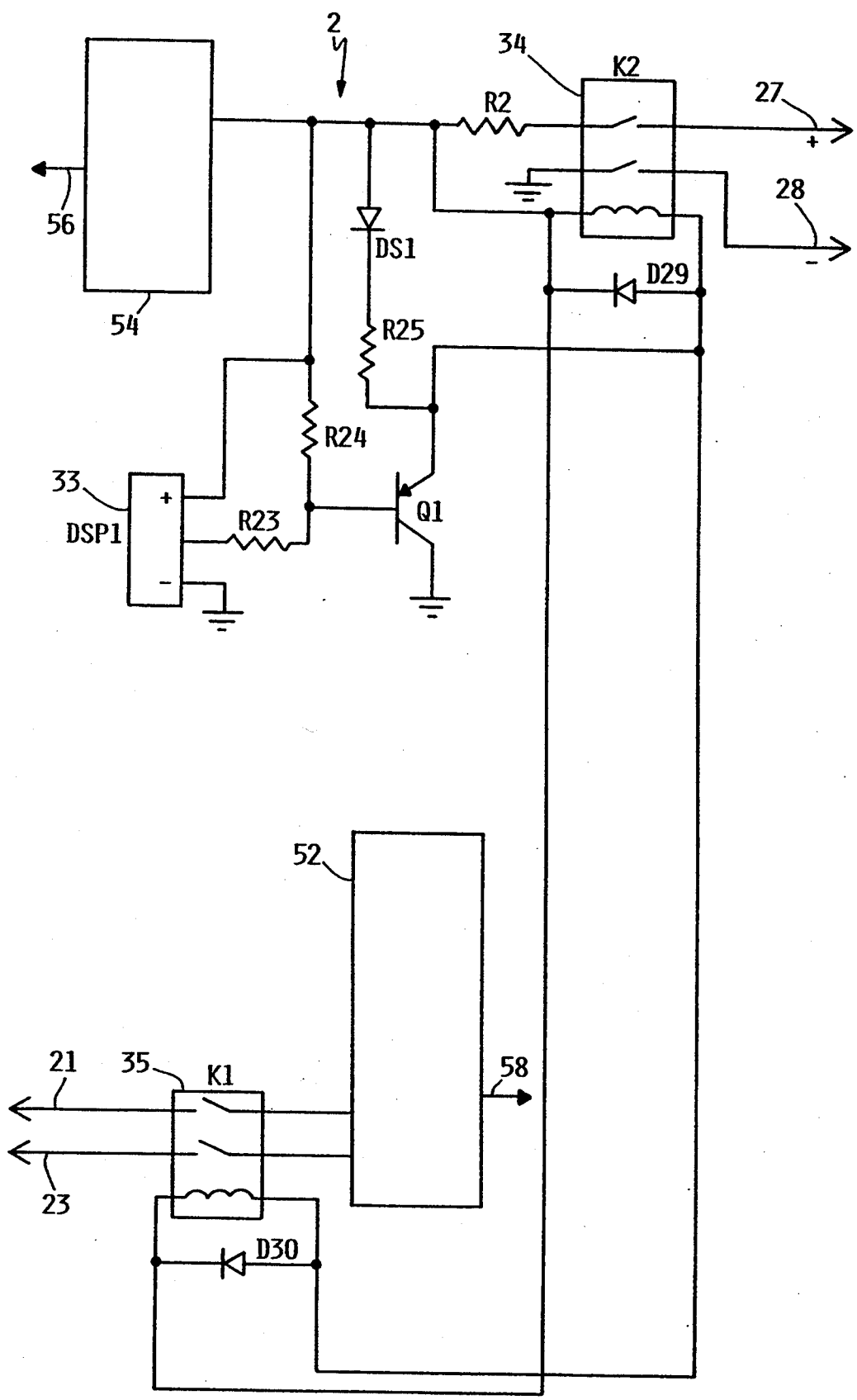
FIG. 5 is a electrical circuit schematic detailing the safety switching circuitry and its relationship to functional elements of the medical device.

FIG. 5 is detail of the circuit schematic of a preferred embodiment utilizing the magneto-resistive element 33 to control normally open relays 34 and 35. The relays are 2 pole normally open contact type devices, model JWD-171-23 relays commercially available from Potter and Brumnfield, Chicago Ill. The relays are separated electrically for assured isolation.

Relay 34 controls the charging circuit, which electrically connects charging contacts 27 and 28 with power supply 54. Supply 54 is connected to a external source of electrical power at 56.

Relay 35 controls the information circuit, which electrically connects contacts 21 and 22 with processing and control system 52. System 52 can be connected to external equipment such as a printer or a personal computer at 58.

Relays 34 and 35 are controlled by a single sensor component 33, although multiple combinations of sensor component 33 and actuator 36 can be provided to add a variety of safety or communications features, or both, to the electrical circuitry.

Relay 34 is positioned electrically and physically close to contacts 25 and 26 and relay 35 is positioned electrically and physically close to contacts 21 and 23 to minimize cross-talk and leakage current from other parts of the electrical circuitry. Table 1 is the component listing of FIG. 5.

TABLE 1

DS1—Panasonic LED LN28RP
D29, D30—1N4148 Diode
DSP1—Honeywell 2SSP Sensor
K1, K2—Potter and Brumnfield JWD-171-23 Relay
Q1—Philips MPSA56PH Transistor
R2—330 ohm Resistor
R23—2.7 K ohm Resistor
R24—100 K ohm Resistor
R25—1.5 K ohm Resistor.

While an electrical isolation safety system has been described for use in the printer/charger module 2, it is within the scope of the present invention to provide a complementary or supplementary electrical isolation safety system in the display module 1. Sensors and actuator can be provided in the opposite modules to the positions shown in FIG. 3 for duplicative or supplementary effect for isolation of the exposed contacts of the portable diagnostic device for further safety precaution.

The scope of the invention is identified in the following claims.

What is claimed is:

1. An apparatus for electrical isolation from a power source of exposed electrical contacts on multiple modules of an electrical device, wherein the isolation continues until proper alignment of the multiple modules, wherein the device comprises two modules capable of mechanical alignment and electrical connection, and wherein at least one module is portable, the apparatus comprising:
unenergized, exposed electrical contacts on the first module,
at least one concealed actuating component within the first module,
at least one concealed sensor component within the second module,
unenergized, exposed electrical contacts on the second module, and
at least one electrical switching device in electrical communication with a corresponding concealed sensor component and with the power source,
wherein each switching device is normally open but when closed is in electrical communication with corresponding exposed electrical contacts on the second module and in energized electrical communication with electrical circuitry connected to the power source,
wherein alignment of a concealed actuating component and a corresponding concealed sensor component causes a corresponding switching device to close and to provide energized electrical communication with electrical circuitry to the exposed electrical contacts on the second module, and
wherein mechanical alignment of the first module and the second module causes energized electrical connection of exposed electrical contacts on the second module with corresponding exposed electrical contacts on the first module.

2. The apparatus according to claim 1, wherein each sensor component is a magneto-resistive position sensor, wherein each actuating component is a magnet, and wherein the alignment is a magnetic alignment.

3. The apparatus according to claim 1, wherein each electrical circuitry switching device comprises an electrical relay.

4. The apparatus according to claim 3, wherein each electrical relay is electrically connected to an exposed electrical contact when the electrical isolation ceases because of alignment of an actuating component and a sensor component that causes a corresponding relay that is normally open to close.

5. The apparatus according to claim 1, wherein the electrical circuitry communicates information between the first module and the second module when the electrical isolation ceases and when the two modules are in mechanical alignment and electrical communication.

6. The apparatus according to claim 1, wherein the apparatus comprises multiple actuator components and multiple sensor components.

7. The apparatus according to claim 1, wherein each sensor component comprises a magnetic Hall-effect sensor or a reed switch, wherein the actuating component is a magnet, and wherein the alignment is a magnetic alignment.

8. The apparatus according to claim 1, wherein each sensor component is an optical switch, wherein each actuating component is a light emitting diode, and wherein the alignment is an optical alignment.

9. The apparatus according to claim 1, wherein each sensor component and each actuating component comprise a magneto-dynamic transformer coupling.

10. The apparatus according to claim 1, wherein each sensor component and each actuating component comprise an electro-static capacitive coupling.

11. The apparatus according to claim 1, wherein each sensor component and each actuating component comprise an electro-dynamic capacitive coupling.

12. The apparatus according to claim 1, wherein each sensor component and each actuating component comprise a radio frequency coupling.

13. The apparatus according to claim 1, wherein the electrical device is a medical device.

14. The apparatus according to claim 1, wherein the medical device is a handheld diagnostic device.

15. An electrical circuit for electrical isolation from a power source of exposed electrical contacts on multiple modules of an electrical device, wherein the device comprises two modules capable of mechanical alignment and electrical connection, wherein at least one module is portable the electrical circuit comprising:
unenergized, exposed electrical contacts on the first module,
unenergized, exposed electrical contacts on the second module;
at least one electrical switching device normally open and interposed between the power source and the exposed electrical contacts on the second module;
at least one concealed sensor component within the second module in electrical communication with the electrical switching device;
at least one concealed actuating component in the first module;
wherein each electrical switching device closes when a corresponding concealed sensor component reacts to an alignment of a corresponding concealed actuating component when the first and second modules are brought into mechanical alignment;
wherein each closed electrical switching device is in energized electrical communication with electrical circuitry connected to the power source and in energized electrical communication with corresponding exposed electrical contacts on the second module for energized electrical communication with the exposed electrical contacts on the first module.

16. The electrical circuitry according to claim 15, wherein each electrical circuitry switching device comprises an electrical relay.

17. The electrical circuitry according to claim 16, wherein the electrical circuitry communicates information between the first module and the second module when the electrical isolation ceases and when the two modules are in mechanical alignment and electrical communication.

* * * * *

UNITED STATES PATENT AND TRADEMARK OFFICE
CERTIFICATE OF CORRECTION

PATENT NO.: 5,411,534

DATED: May 2, 1995

INVENTOR(S): Dieken et al.

It is certified that error appears in the above-identified patent and that said Letters Patent is hereby corrected as shown below:

Column 6:

In Claim 1, line 5, please replace "two modules" with --a first module and a second module--.
   Column 8:
In Claim 15, line 4, please replace "two modules" with --a first module and a second module--.

Signed and Sealed this

Seventeenth Day of September, 1996

Attest:

BRUCE LEHMAN

Attesting Officer

Commissioner of Patents and Trademarks